(12) United States Patent
Kirszenblat et al.

(10) Patent No.: US 11,013,416 B2
(45) Date of Patent: May 25, 2021

(54) MEASURING RESPIRATION WITH AN IN-EAR ACCELEROMETER

(71) Applicant: Bose Corporation, Framingham, MA (US)

(72) Inventors: Romain Kirszenblat, Allston, MA (US); Mikhail Ioffe, Newton, MA (US)

(73) Assignee: Bose Corporation, Framingham, MA (US)

( * ) Notice: Subject to any disclaimer, the term of this patent is extended or adjusted under 35 U.S.C. 154(b) by 130 days.

(21) Appl. No.: 15/881,034

(22) Filed: Jan. 26, 2018

(65) Prior Publication Data
US 2019/0231197 A1 Aug. 1, 2019

(51) Int. Cl.
| | | |
|---|---|---|
| *A61N 1/37* | (2006.01) | |
| *A61B 5/0205* | (2006.01) | |
| *A61B 5/11* | (2006.01) | |
| *H04R 1/10* | (2006.01) | |
| *A61B 5/00* | (2006.01) | |
| *A61B 5/024* | (2006.01) | |
| *A61B 5/08* | (2006.01) | |

(52) U.S. Cl.
CPC ........ *A61B 5/0205* (2013.01); *A61B 5/02444* (2013.01); *A61B 5/1102* (2013.01); *A61B 5/6803* (2013.01); *A61B 5/6815* (2013.01); *A61B 5/7257* (2013.01); *A61B 5/7278* (2013.01); *H04R 1/1016* (2013.01); *H04R 1/1041* (2013.01); *H04R 1/1075* (2013.01); *H04R 1/1083* (2013.01); *A61B 5/02438* (2013.01); *A61B 5/0816* (2013.01); *A61B 2560/0462* (2013.01); *A61B 2562/0219* (2013.01); *A61B 2562/166* (2013.01)

(58) Field of Classification Search
USPC .......................................................... 607/17
See application file for complete search history.

(56) References Cited

U.S. PATENT DOCUMENTS 5,143,078 A  9/1992  Mather et al.
7,850,619 B2  12/2010  Gavish et al.
(Continued)

FOREIGN PATENT DOCUMENTS

GB      2532745 A    6/2016
WO   2010054863 A1   5/2010
(Continued)

OTHER PUBLICATIONS

International Search Report and Written Opinion dated Jul. 3, 2019 for PCT/US2019/014066.
(Continued)

*Primary Examiner* — Nicole F Lavert
(74) *Attorney, Agent, or Firm* — Bose Corporation

(57) ABSTRACT

An earphone includes a loudspeaker, a microphone, a housing supporting the loudspeaker and microphone, and an ear tip surrounding the housing and configured to acoustically couple both the loudspeaker and the microphone to an ear canal of a user, and to acoustically close the entrance to the user's ear canal. A processor receives input audio signals from the microphone, detects peaks having a frequency of around 1 Hz in the input audio signals, based on the detected peaks, computes an instantaneous heart rate, measures a frequency of an oscillation within the instantaneous heart rate, and based on the frequency of the oscillation, computes a rate of respiration.

17 Claims, 6 Drawing Sheets

(56) References Cited

U.S. PATENT DOCUMENTS

| | | |
|---|---|---|
| 9,635,452 B2 | 4/2017 | Cheng et al. |
| 2002/0091049 A1 | 7/2002 | Hisano et al. |
| 2004/0077934 A1 | 4/2004 | Massad |
| 2007/0118011 A1 | 5/2007 | Harrison et al. |
| 2008/0146890 A1 | 6/2008 | LeBoeuf et al. |
| 2008/0171945 A1 | 7/2008 | Dotter |
| 2009/0143636 A1 | 6/2009 | Mullen |
| 2010/0125218 A1 | 5/2010 | Haartsen et al. |
| 2010/0240945 A1 | 9/2010 | Bikko |
| 2011/0295083 A1 | 12/2011 | Doelling et al. |
| 2012/0203077 A1 | 8/2012 | He et al. |
| 2012/0225412 A1 | 9/2012 | Wagner |
| 2012/0256933 A1 | 10/2012 | Airey et al. |
| 2013/0034258 A1 | 2/2013 | Lin |
| 2013/0090567 A1 | 4/2013 | Lee et al. |
| 2014/0141395 A1 | 5/2014 | Gavish et al. |
| 2015/0150515 A1 | 6/2015 | Strachan |
| 2015/0258301 A1 | 9/2015 | Trivedi et al. |
| 2015/0351688 A1 | 12/2015 | Just et al. |
| 2017/0325718 A1 | 11/2017 | Boesen et al. |
| 2017/0347177 A1 | 11/2017 | Masaki et al. |
| 2017/0367658 A1 | 12/2017 | LeBoeuf et al. |
| 2018/0338193 A1 | 11/2018 | Wallace et al. |
| 2019/0022349 A1 | 1/2019 | Kirszenblat et al. |
| 2019/0028789 A1 | 1/2019 | Stockton et al. |
| 2019/0212198 A1* | 7/2019 | Marsh .................. A61B 5/01 |

FOREIGN PATENT DOCUMENTS

| | | |
|---|---|---|
| WO | 2017011431 A2 | 1/2017 |
| WO | 2017068571 A1 | 4/2017 |
| WO | 2017203251 A1 | 11/2017 |

OTHER PUBLICATIONS

Invitation to Pay Additional Fees and Partial International Search Report dated May 2, 2019 for PCT/US2019/014066.
International Search Report and Written Opinion dated Oct. 10, 2018 for International application No. PCT/US2018/043058.
International Search Report and Written Opinion dated Oct. 10, 2018 for International application No. PCT/ US2018/043061.
International Search Report and Written Opinion dated Oct. 10, 2018 for International application No. PCT/US2018/043062.
Axel Schäfer et al: "Estimation of Breathing Rate from Respiratory Sinus Arrhythmia: Comparison of Various Methods", Annals of Biomedical Engnieering, Kluwer Academic Publishers-Plenum Publishers, NE, vol. 36, No. 3, Jan. 11, 2008 (Jan. 11, 2008), pp. 476-485, XP019568785, ISSN: 1573-9686, pp. 476-p. 480.
Richard Singhathip et al: "Extracting Respiration Rate From Raw ECG Signals", Biomedical Engineering: Applications, Basis and Communications = Yixue-Gongc, World Scientific, TW, vol. 22, No. 4, Aug. 1, 2010 (Aug. 1, 2010), pp. 307-314, XP008169483, ISSN : 1016-2372, DOI: 10.4015/S1016237210002079 pp. 307-p. 309.
Kim J M et al: "Two Algorithms for Detecting Respiratory Rate from ECG Signal", Imaging the Future Medicine : World Congress on Medical Physics and Biomedical Engineering 2006, Aug. 27-Sep. 1, 2006, Coex Seoul, K; [IFMBE Proceedings, Vol . 14], Springer, DE, vol. 14, Jan. 1, 2007 (Jan. 1, 2007), pp. 4069-4071, XP008169469, DOI: 10 .1007/978-3-540-36841-0 1030 ISBN : 978-3-540-36839-7—the whole document.
Insternational Search Report and Written Opinion dated Apr. 26, 2019 for PCT/US20191014772.

\* cited by examiner

MEASURING RESPIRATION WITH AN IN-EAR ACCELEROMETER

RELATED APPLICATIONS

This application is related to, and incorporates by reference, U.S. patent application Ser. No. 15/106,989, filed Jun. 21, 2016; application Ser. No. 15/348,400, filed Nov. 10, 2016; and application Ser. No. 15/352,034, filed Nov. 17, 2016, all titled Intelligent Earplug System. It is also related to U.S. patent application Ser. No. 15/267,567, entitled Sleep Assistance Device; application Ser. No. 15/267,464, entitled Sleep Quality Scoring and Improvement; application Ser. No. 15/267,552, entitled Intelligent Wake-Up System; application Ser. No. 15/267,848, entitled Sleep System; application Ser. No. 15/267,858, entitled User Interface for a Sleep System; and application Ser. No. 15/267,886, entitled Sleep Assessment Using a Home Sleep System, all of which were filed on Sep. 16, 2016. It is also related to U.S. patent application Ser. No. 15/655,836, titled Sleep Assistance Device For Multiple Users, and Ser. Nos. 15/655,845, 15/655,853, and 15/655,857, all titled Earphones for Measuring and Entraining Respiration, filed Jul. 20, 2017, and incorporated here by reference.

BACKGROUND

This disclosure relates to earphones for measuring and entraining respiration.

Sleeplessness and poor or interrupted sleep may significantly affect a person's health. Poor sleep may be caused by such factors as ambient noise, stress, medical conditions, or discomfort. Thus, there exists a need for a sleep aid that can help address the underlying causes of poor sleep without adversely affecting the user's health in other, unintended ways.

SUMMARY

In general, in one aspect, a system includes an earphone with a loudspeaker, an accelerometer, a housing supporting the loudspeaker and accelerometer, and an ear tip surrounding the housing and configured to acoustically couple the loudspeaker to an ear canal of a user, and a processor. The processor receives input signals from the accelerometer in response to motion of the earphone, and detects peaks in the input signals. Based on the detected peaks, the processor computes an instantaneous heart rate, measures a frequency of an oscillation within the instantaneous heart rate, and based on the frequency of the oscillation, computes a rate of respiration.

Implementations may include one or more of the following, in any combination. The accelerometer may be located on a circuit board within the earphone. The housing may include an outer shell of the earphone, and the accelerometer may be located in the outer shell. The input signals may include acceleration measurements for each of three axes, and the processor may detect the peaks by combining the three acceleration measurements into the norm of the three measurements. The processor may receive second input signals from a second accelerometer in a second earphone, including second acceleration measurements for each of three axes of the second accelerometer, combine the second three acceleration measurements into the norm of the second three measurements, detect the peaks by combining the norm of the three measurements from the first accelerometer with the norm of the three measurements from the second accelerometer, and detect peaks within the result of the combination. Combining the norms may include multiplying the amplitude of the norm of the first three acceleration measurements by the amplitude of the norm of the second three acceleration measurements, at each time that the two accelerometers' measurements are sampled. The processor may adjust output audio signals based on the rate of respiration, and provide the output audio signals to the loudspeaker.

Adjusting the output audio signals may include adjusting a rhythm of the output audio signals to be about one cycle per minute less than the detected respiration rate. Adjusting the output audio signals may include transitioning the output audio signals from respiration entrainment sounds to masking sounds. Adjusting the output audio signals may include transitioning the output audio signals from masking sounds to awakening sounds. The earphone may include a memory storing sound files, and providing the output audio signals may include retrieving a first sound file from the memory. Adjusting the output audio signals may include retrieving a second sound file from the memory and using the second sound file to generate the output audio signal.

The processor may be integrated within the earphone. The processor may be integrated within a portable computing device. The processor may measure the frequency of the oscillation within the instantaneous heart rate by computing a fast Fourier transform (FFT) of the instantaneous heart rate. The processor may measure the frequency of the oscillation within the instantaneous heart rate by computing a gradient of the instantaneous heart rate, and computing a fast Fourier transform (FFT) of the gradient of the instantaneous heart rate. The processor may measure the frequency of the oscillation within the instantaneous heart rate by detecting peaks of the instantaneous heart rate. The processor may measure the frequency of the oscillation within the instantaneous heart rate by fitting a sine function to the instantaneous heart rate, the frequency of the sine being the frequency of the oscillation. The ear tip may be configured to acoustically close the entrance to the user's ear canal.

In general, in one aspect, measuring the respiration rate of a user of an earphone includes receiving input signals from an accelerometer supported within the earphone, the input signals including acceleration measurements for each of three axes, and, in a processor, combining the three acceleration measurements into the norm of the three measurements, detecting peaks in the norm of the accelerometer measurements, based on the detected peaks, computing an instantaneous heart rate, measuring a frequency of an oscillation within the instantaneous heart rate, and based on the frequency of the oscillation, computing a rate of respiration.

Implementations may include one or more of the following, in any combination. Measuring the frequency of the oscillation within the instantaneous heart rate may include computing a fast Fourier transform (FFT) of the instantaneous heart rate. Measuring the frequency of the oscillation within the instantaneous heart rate may include computing a gradient of the instantaneous heart rate, and computing a fast Fourier transform (FFT) of the gradient of the instantaneous heart rate. Measuring the frequency of the oscillation within the instantaneous heart rate may include detecting peaks of the instantaneous heart rate. Measuring the frequency of the oscillation within the instantaneous heart rate may include fitting a sine function to the instantaneous heart rate, the frequency of the sine being the frequency of the oscillation. Second input acceleration signals may be received from a second accelerometer supported within a second earphone, the second input signals including acceleration measurements for each of three axes of the second accelerometer; the processor may detect the peaks by combining the second three acceleration measurements into the norm of the second three measurements, combining the norm of the first three acceleration measurements with the norm of the second three acceleration measurements, and detecting peaks within the result of the combination.

Advantages include sensing the respiration rate at the ear without interference from audio signals being generated by the earphone, and without a need to seal the ear interface.

All examples and features mentioned above can be combined in any technically possible way. Other features and advantages will be apparent from the description and the claims.

DESCRIPTION

Several of the above-referenced applications describe a bedside system that detects a user's respiration rate and uses that to infer and manage their sleep state. In particular, to assist the user with falling to sleep, the system plays sounds that have a rhythm slightly slower than the user's own respiration rate. This naturally leads the user to slow their breathing to match the rhythm of the sounds, in a process referred to as entrainment. As the user slows their rate of respiration, the rate of the sounds is further reduced, in a feedback loop that leads the user gradually to sleep. Once the user falls asleep (as indicated by artifacts in their respiration rate), the system switches to playing masking sounds, which diminish the user's ability to detect, and be disturbed by, external sounds. If the user is detected to be waking up too early, entrainment may be reactivated. When it is time for the user to wake up, the system may coordinate wake-up sounds with the user's sleep state and other information to wake the user in the least-disruptive way possible.

Others of the above-referenced applications describe intelligent earplugs which the user can wear while sleeping, and which provide masking sounds through the night, and alarm or alert sounds when needed. These earplugs are controlled by a smartphone, but principally operate autonomously, playing stored masking sounds until instructed otherwise by the controlling phone, or based on an internal clock. It would be advantageous if the intelligent earplugs could play the respiration-entraining sounds of the bedside systems, to help the user fall asleep without disturbing others who may be sharing the bed or room. One solution to that, described in co-pending application Ser. No. 15/655,836, is for the sleep system to inform the earplugs of the user's respiration rate and sleep state, and for the earplugs to adjust the rate of a rhythmic component in stored entrainment sounds as in the out-loud system.

The Ser. Nos. 15/655,853 and 15/655,857 applications describe how to add respiration sensing to the earplugs themselves, using microphones, so that the external system is not required, and the earplugs can operate fully autonomously, or with only a smart phone to control them.

The technique described in the '853 application, of using a microphone to measure heart rate variability, and from that deriving respiration rate, can also be performed using an accelerometer, as described below.

Figure 1:
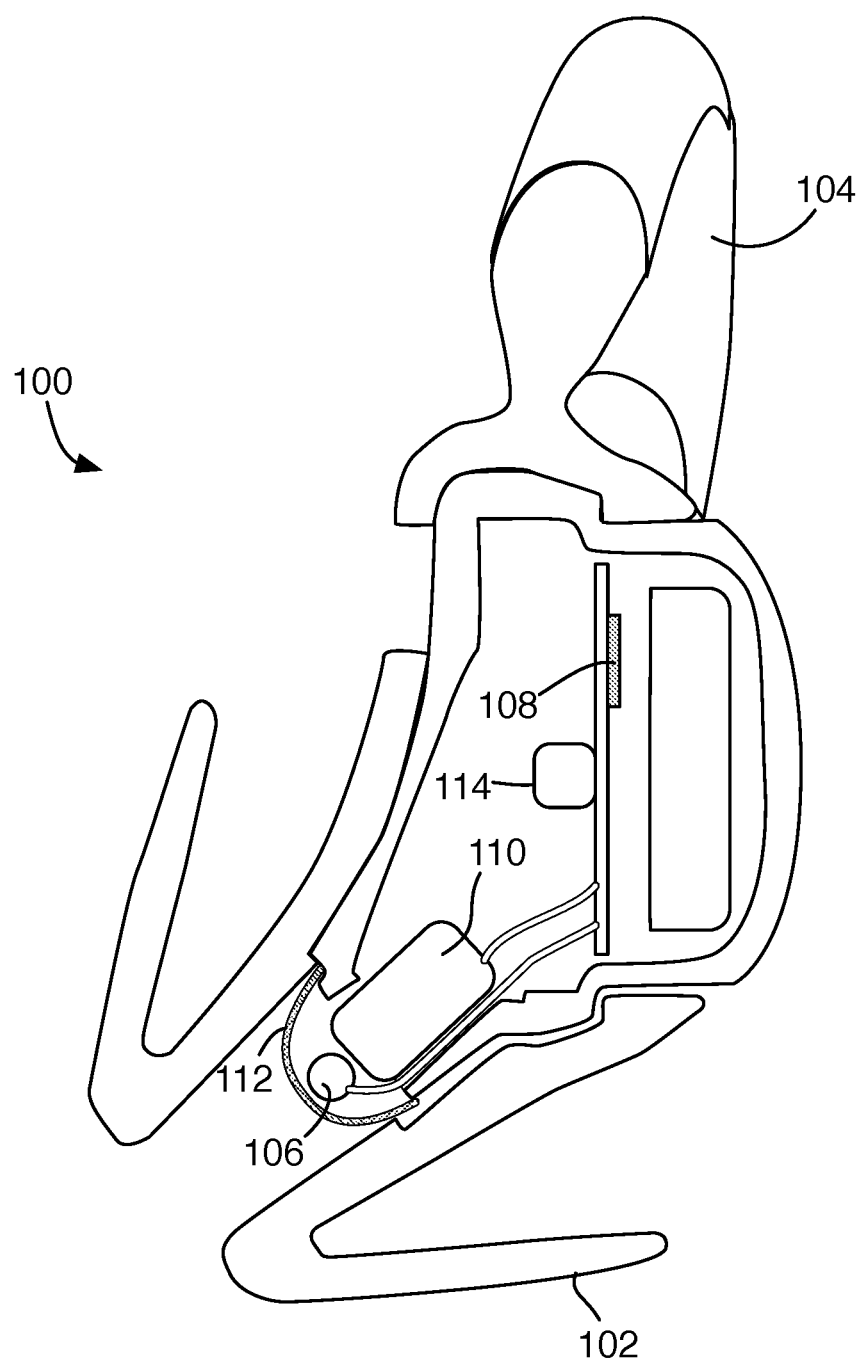
FIGS. 1 and 2 show cross-sectional views of earphones with an integrated accelerometer.
Figure 2:
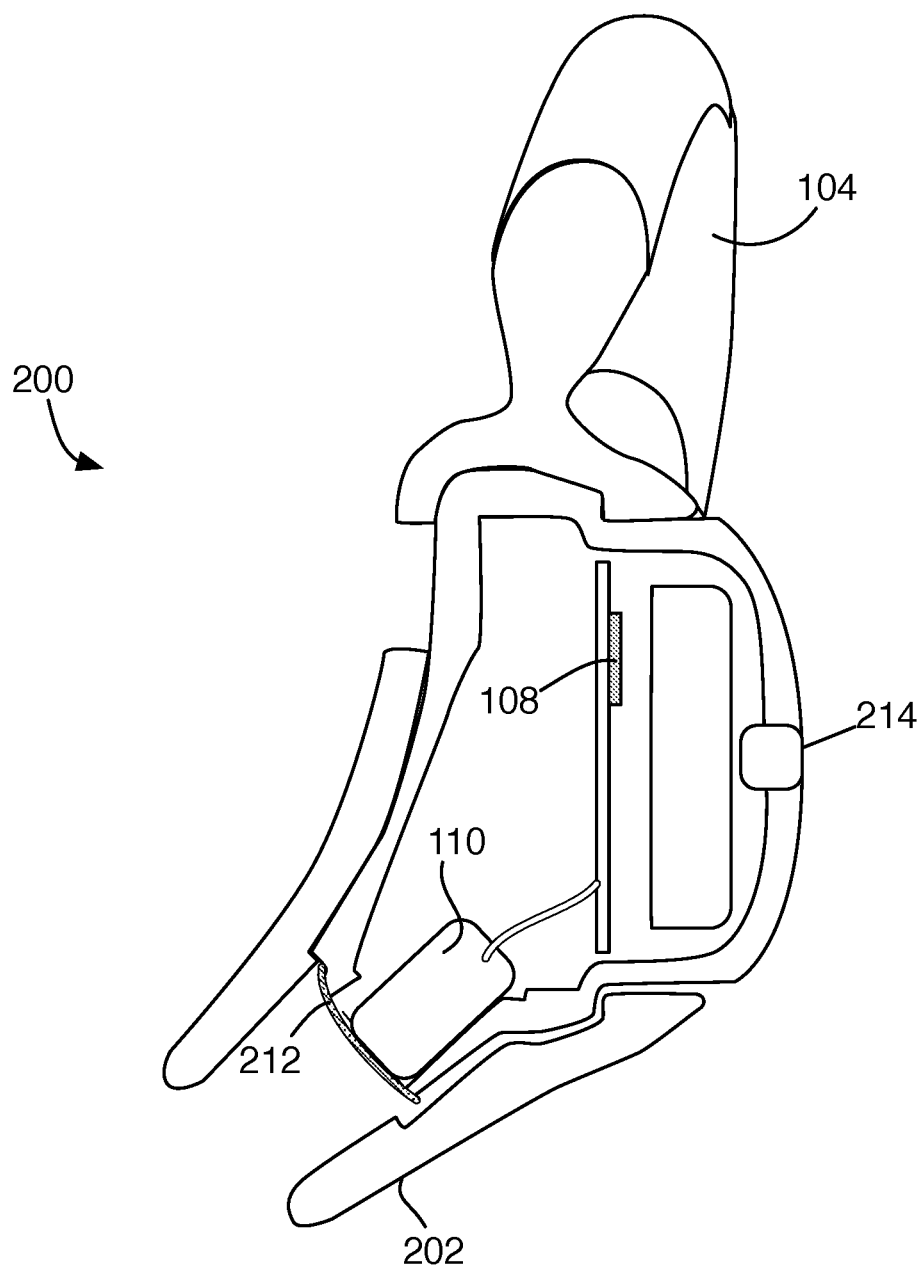
Figure 3:
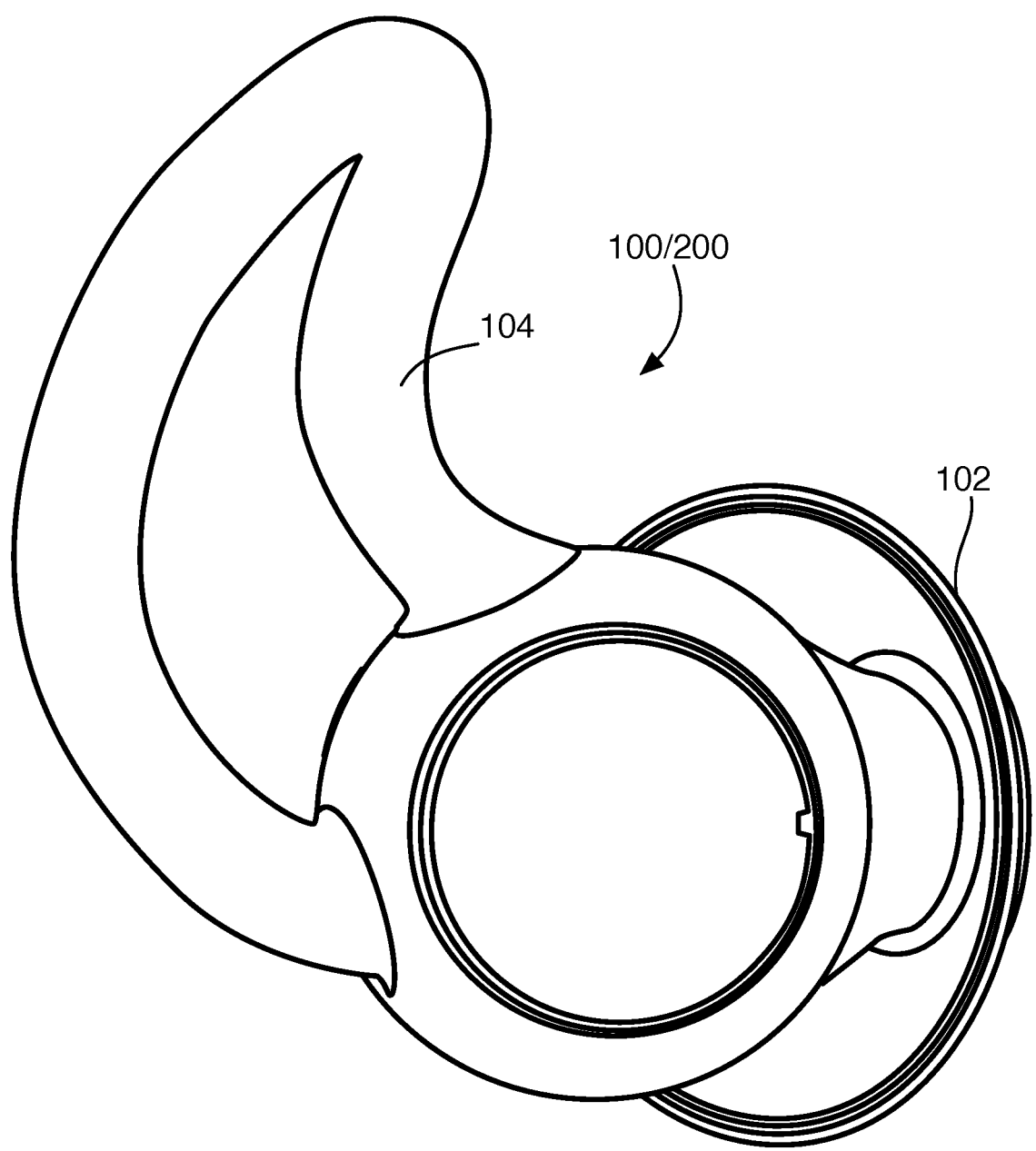
FIG. 3 shows an external view of the system of FIG. 1 or 2.
Figure 4A:
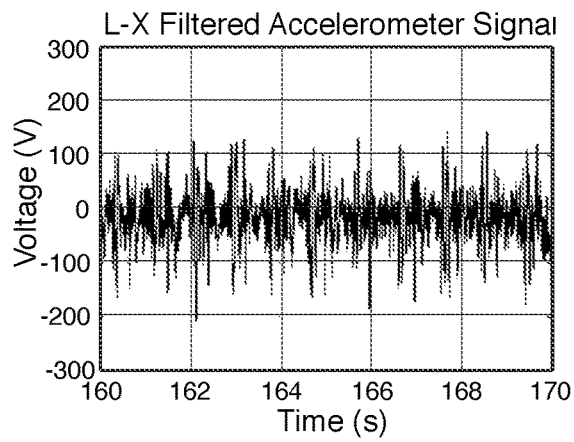
FIGS. 4A, 4B, 4C, 4D, 4E, 4F, 5A, 5B, 6, and 7 show graphs of sensor readings
Figure 4B:
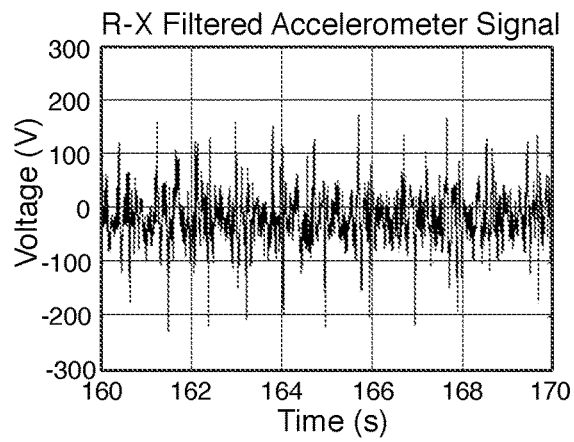
Figure 4C:
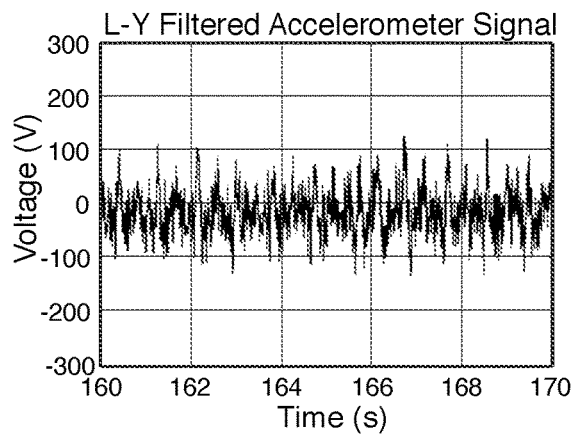
Figure 4D:
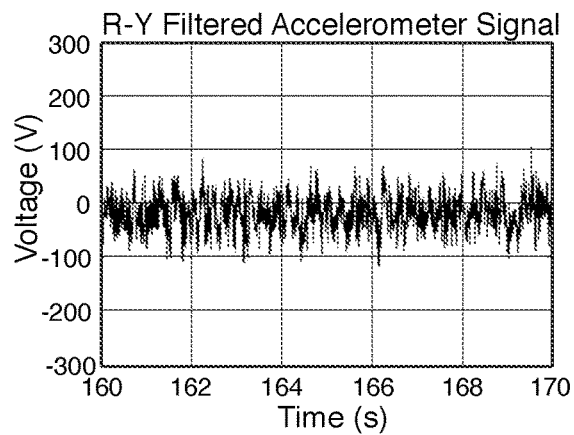
Figure 4E:
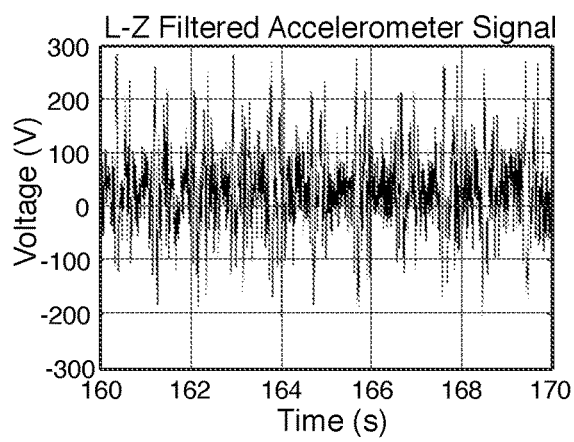
Figure 4F:
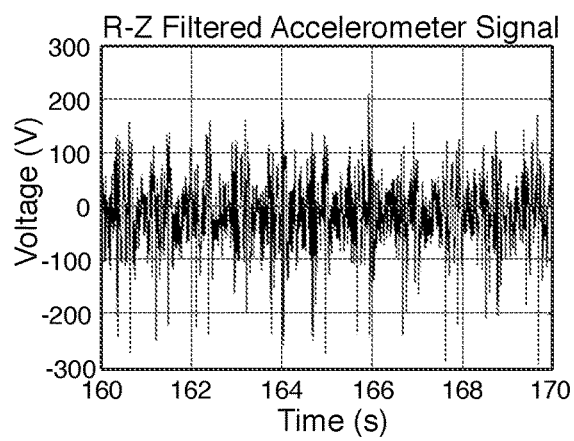

As shown in FIGS. 1 and 3, sleep-sensing earphones 100 include an ear tip sealing structure 102 that blocks, or occludes, the entrance to the ear canal. The earphones 200 in FIG. 2 omit the sealing structure 102, having instead an ear tip structure 202 that merely seats the earphone in the ear, without sealing the canal entrance. Aside from the different sealing structures, FIGS. 1 and 2 show cross-sections of two different earphone examples, while FIG. 3 shows an exterior view, for reference. The example of FIG. 3 uses the sealing structure 102 from FIG. 1, but the earbud of FIG. 2 would have similar appearance. A retaining structure 104 helps retain the earphone in the ear, and puts pressure on the sealing structure 102, if present, to maintain the seal by pushing on the concha, opposite to where the sealing structure meets the ear canal. The sealing structure 102 helps to passively block outside sounds from entering the ear, increasing the effectiveness of the masking sounds played by the earphones.

In the example of FIG. 1, an accelerometer 114 is located on the circuit board of earphone 100. In the example of FIG. 2, an accelerometer 214 is located in the outer shell of the earphone 200. In both examples, the accelerometer is able to detect motion of the earphone caused by the user's heartbeat, using the principles of ballistocardiography. Unlike techniques using a microphone, the accelerometer 114/214 can produce a usable signal without having to seal the ear canal, and can be located anywhere on the earphone, as demonstrated by these two examples. The processor 108 on-board each earphone (or in one, if they coordinate their action) can then extract the respiration rate from the accelerometer output, and adjust the timing of entrainment sounds being played to the user through a speaker 110. In the example of FIG. 1, the microphone is still present, for use in other functions, such as providing active noise cancellation or voice interface input.

The heartbeat is derived from the accelerometer signals, and the respiration rate is derived from the heart rate variability (HRV). FIGS. 4A-4F show the output accelerometer signals for three axes, as reported by accelerometers in both the left and right ears, filtered using a third-order Butterworth low-pass filter with a cutoff frequency of 50 Hz. The user's pulse is present in all six signals, but the signal to noise ratio (SNR) is not very high. In particular, in this example, the X and Z axes (4A, 4B, 4E, 4F) have much better SNR than the Y axis (4C and 4D, where the pulse is barely visible), but neither of them would easily yield the heart rate. In other examples, depending on the precise orientation of the earphones in the ears of the user, different axes could have a better or worse SNR on another user. Because the goal is to obtain the beat-to-beat heart rate, time average methods cannot be used to filter out the noise.

Instead of separately using the axes, we can combine the three axes of each ear into their norm:

$$N=\sqrt{x^2+y^2+z^2} \tag{1}$$

Figure 5A:
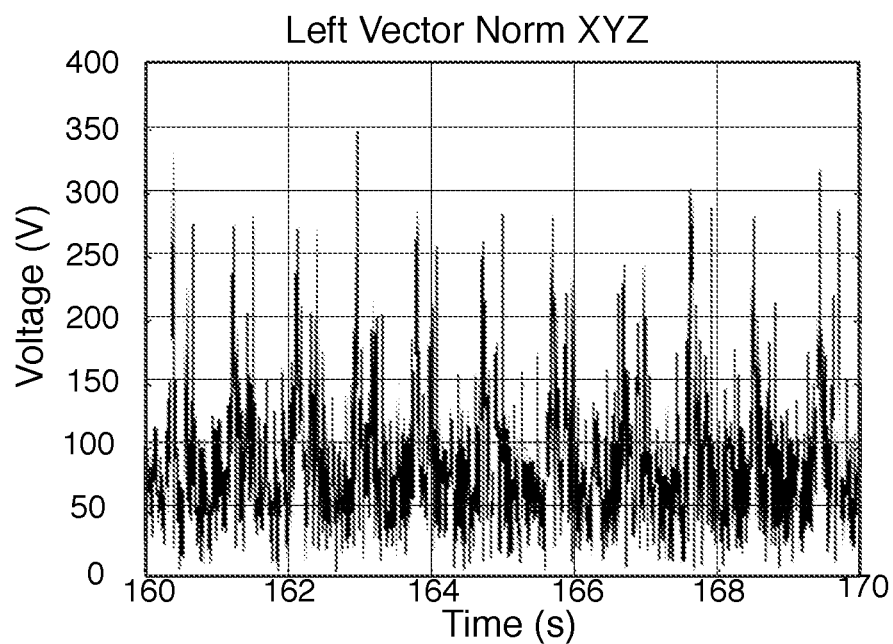
Figure 5B:
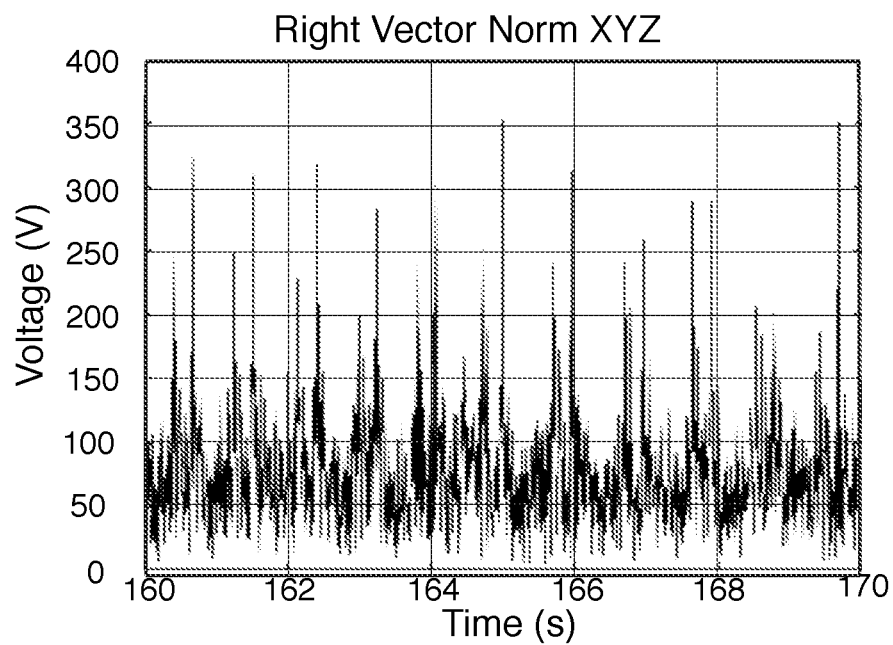

Graphs of the two norms, one for each ear, are shown in FIGS. 5A and 5B. Using the norm of the three axes not only improves the SNR, but also immunizes the reading to the exact orientation of the earphone in the user's ear. Other methods of combining the signals from the three axes may also be used.

Figure 6:
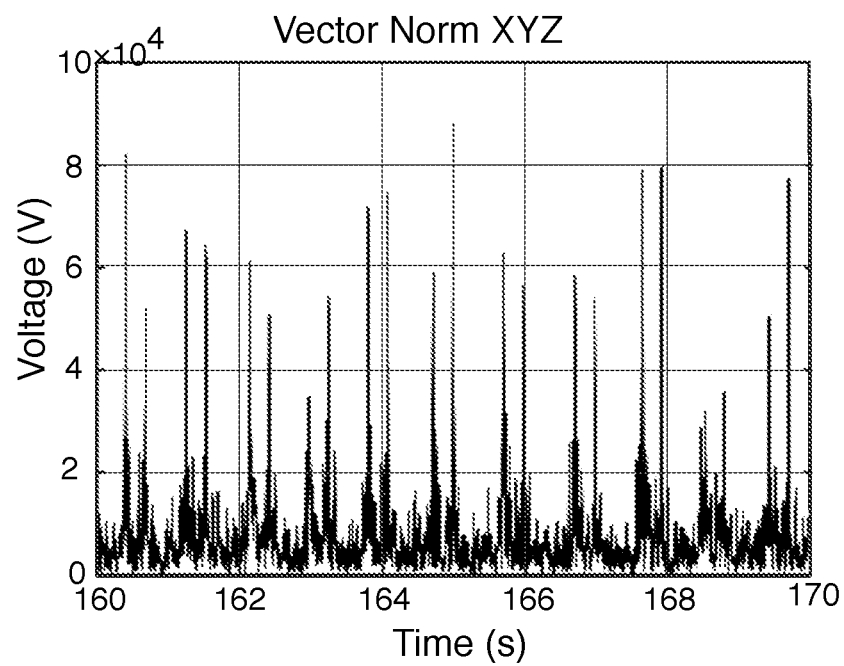

Combining the amplitudes of the two signals at each time sample, such as by multiplication, can greatly increase the signal to noise ratio, as shown in FIG. 6. Note that each beat is represented by two peaks close to each other. Various standard de-duplicating procedures, such as envelope fitting, can be used to combine the peaks or otherwise manage the duplication.

Figure 7:
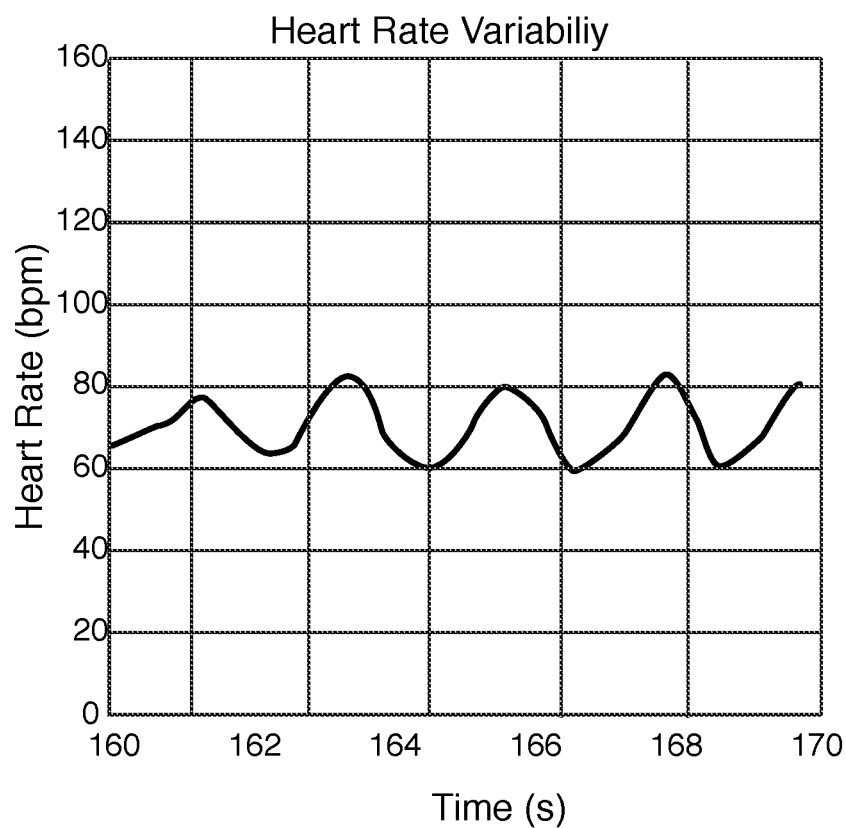

Applying a peak-finding algorithm to the combined accelerometer signals and observing the distance between consecutive peaks yields the beat-to-beat, or instantaneous, heart rate value, shown in FIG. 7. Note that the peaks in the curve in FIG. 7 do not map to the pairs of peaks in FIG. 6—the shape of the curve in FIG. 7 shows the variability in the distance between the pairs of peaks in FIG. 6.

FIG. 7 shows that there is a cyclic variability to the instantaneous heart rate. The period of this variability happens to be the respiration rate—as the user inhales, their heart rate increases, and as they exhale, their heart rate decreases. Applying another peak detection step, or other frequency analysis such as a fast Fourier transform (FFT) or fitting a sine to the curve, to the instantaneous heart rate or to its gradient, reveals the respiration rate.

Embodiments of the systems and methods described above comprise computer components and computer-implemented steps that will be apparent to those skilled in the art. For example, it should be understood by one of skill in the art that the computer-implemented steps may be stored as computer-executable instructions on a computer-readable medium such as, for example, hard disks, optical disks, solid-state disks, flash ROMS, nonvolatile ROM, and RAM. Furthermore, it should be understood by one of skill in the art that the computer-executable instructions may be executed on a variety of processors such as, for example, microprocessors, digital signal processors, and gate arrays. For ease of exposition, not every step or element of the systems and methods described above is described herein as part of a computer system, but those skilled in the art will recognize that each step or element may have a corresponding computer system or software component. Such computer system and software components are therefore enabled by describing their corresponding steps or elements (that is, their functionality), and are within the scope of the disclosure.

A number of implementations have been described. Nevertheless, it will be understood that additional modifications may be made without departing from the scope of the inventive concepts described herein, and, accordingly, other embodiments are within the scope of the following claims.

What is claimed is:
1. A system comprising:
an earphone comprising:
   a loudspeaker;
   an accelerometer;
   a housing supporting the loudspeaker and accelerometer; and
   an ear tip surrounding the housing and configured to acoustically couple the loudspeaker to an ear canal of a user;
a second earphone comprising:
   a second loudspeaker;
   a second accelerometer;
   a second housing supporting the second loudspeaker and second accelerometer; and
   a second ear tip surrounding the second housing and configured to acoustically couple the second loudspeaker to a second ear canal of the user;
and
a processor configured to:
   receive input signals from the accelerometer in response to motion of the earphone;
   detect peaks in the input signals;
   based on the detected peaks, compute an instantaneous heart rate;
   measure a frequency of an oscillation within the instantaneous heart rate; and
   based on the frequency of the oscillation, compute a rate of respiration,
wherein the input signals comprise acceleration measurements for each of three axes, and the processor is configured to detect the peaks by combining the three acceleration measurements into a norm of the three measurements, and
wherein the processor is further configured to:
   receive second input signals from the second accelerometer comprising second acceleration measurements for each of three axes of the second accelerometer;
   combine the second three acceleration measurements into the norm of the second three measurements; and
   detect the peaks by combining the norm of the three measurements from the first accelerometer with the norm of the three measurements from the second accelerometer and detecting peaks within the result of the combination.

2. The system of claim 1, wherein the accelerometer is located on a circuit board within the earphone.

3. The system of claim 1, wherein the housing comprises an outer shell of the earphone, and the accelerometer is located in the outer shell.

4. The system of claim 1, wherein combining the norms comprises multiplying the amplitude of the norm of the first three acceleration measurements by the amplitude of the norm of the second three acceleration measurements, at each time that the two accelerometers' measurements are sampled.

5. The system of claim 1, wherein the processor is further configured to adjust output audio signals based on the rate of respiration, and provide the output audio signals to the loudspeaker.

6. The system of claim 5, wherein adjusting the output audio signals comprises adjusting a rhythm of the output audio signals to be about one cycle per minute less than the detected respiration rate.

7. The system of claim 5, wherein adjusting the output audio signals comprises transitioning the output audio signals from respiration entrainment sounds to masking sounds.

8. The system of claim 5, wherein adjusting the output audio signals comprises transitioning the output audio signals from masking sounds to awakening sounds.

9. The system of claim 5, wherein
the earphone further includes a memory storing sound files; and
providing the output audio signals comprises retrieving a first sound file from the memory.

10. The system of claim 9, wherein adjusting the output audio signals comprises retrieving a second sound file from the memory and using the second sound file to generate the output audio signal.

11. The system of claim 1, wherein the processor is integrated within the earphone.

12. The system of claim 1, wherein the processor is integrated within a portable computing device.

13. The system of claim 1, wherein the processor is configured to measure the frequency of the oscillation within the instantaneous heart rate by computing a fast Fourier transform (FFT) of the instantaneous heart rate.

14. The system of claim 1, wherein the processor is configured to measure the frequency of the oscillation within the instantaneous heart rate by
- computing a gradient of the instantaneous heart rate; and
- computing a fast Fourier transform (FFT) of the gradient of the instantaneous heart rate.

15. The system of claim 1, wherein the processor is configured to measure the frequency of the oscillation within the instantaneous heart rate by detecting peaks of the instantaneous heart rate.

16. The system of claim 1, wherein the processor is configured to measure the frequency of the oscillation within the instantaneous heart rate by fitting a sine function to the instantaneous heart rate, the frequency of the sine being the frequency of the oscillation.

17. The system of claim 1, wherein the ear tip is configured to acoustically close the entrance to the user's ear canal.

\* \* \* \* \*